(12) United States Patent
Konishi et al.

(10) Patent No.: US 9,295,589 B2
(45) Date of Patent: Mar. 29, 2016

(54) WATER DISINTEGRATABLE LEAKPROOF SHEET

(75) Inventors: Takayoshi Konishi, Kagawa (JP); Koichi Yamaki, Kagawa (JP); Azusa Matsushima, Kagawa (JP)

(73) Assignee: Unicharm Corporation, Ehime (JP)

( * ) Notice: Subject to any disclaimer, the term of this patent is extended or adjusted under 35 U.S.C. 154(b) by 204 days.

(21) Appl. No.: 14/008,642

(22) PCT Filed: Feb. 27, 2012

(86) PCT No.: PCT/JP2012/054782
§ 371 (c)(1),
(2), (4) Date: Sep. 30, 2013

(87) PCT Pub. No.: WO2012/132704
PCT Pub. Date: Oct. 4, 2012

(65) Prior Publication Data
US 2014/0025026 A1    Jan. 23, 2014

(30) Foreign Application Priority Data

Mar. 29, 2011 (JP) .................................. 2011-073234

(51) Int. Cl.
*A61F 13/15* (2006.01)
*A61F 13/514* (2006.01)

(52) U.S. Cl.
CPC ..... *A61F 13/15211* (2013.01); *A61F 13/51401* (2013.01); *A61F 13/51478* (2013.01); *A61F 2013/51433* (2013.01)

(58) Field of Classification Search
CPC ............... A61F 13/15211; A61F 13/15219; A61F 13/15235; A61F 13/51417; A61F 13/51433; A61F 13/51401
See application file for complete search history.

(56) References Cited

U.S. PATENT DOCUMENTS

| 7,179,245 | B2 * | 2/2007 | Giori ............................. 604/332 |
| 8,907,155 | B2 * | 12/2014 | Wang et al. .................. 604/364 |
| 2001/0021458 | A1 * | 9/2001 | Campbell et al. ............. 428/508 |
| 2002/0177827 | A1 * | 11/2002 | Noda et al. .................... 604/364 |
| 2004/0147892 | A1 | 7/2004 | Mizutani et al. |
| 2012/0130331 | A1 * | 5/2012 | Wang et al. .................. 604/364 |

FOREIGN PATENT DOCUMENTS

| EP | 2 163 378 A1 | 3/2010 |
| JP | 2001-333933 A | 12/2001 |
| JP | 2007-097924 A | 4/2007 |
| JP | 2008-073356 A | 4/2008 |
| JP | 2009-013521 A | 1/2009 |
| WO | WO 01-66160 A1 | 9/2001 |
| WO | WO 02/094157 A1 | 11/2002 |
| WO | WO 2012/066436 A2 | 5/2012 |

OTHER PUBLICATIONS

International Search Report from corresponding PCT application No. PCT/JP2012/054782 dated May 15, 2012 (2 pgs).

* cited by examiner

*Primary Examiner* — Bradley Philips
(74) *Attorney, Agent, or Firm* — Brinks Gilson & Lione

(57) ABSTRACT

A water disintegratable leak-proof sheet for an absorbent article that has an excellent leak-proof property during wear and excellent water disintegrating property after disposal. The water disintegratable leak-proof sheet of the present disclosure has the following construction. A water disintegratable leak-proof sheet for an absorbent article comprising a water disintegratable base material layer and a water-insoluble and biodegradable resin layer on the water disintegratable base material layer, wherein the tearing strength in the planar direction of the water disintegratable leak-proof sheet is no greater than 0.15 N/40 mm in both a first direction and a second direction perpendicular to the first direction.

17 Claims, 1 Drawing Sheet

WATER DISINTEGRATABLE LEAKPROOF SHEET

RELATED APPLICATION

This application is a 35 U.S.C. §371 national phase filing of International Patent Application No. PCT/JP2012/054782, filed Feb. 27, 2012, through which and to which priority is claimed under 35 U.S.C. §119 to Japanese Patent Application No. 2011-073234, filed Mar. 29, 2011.

TECHNICAL FIELD

The present disclosure relates to a water disintegratable leakproof sheet for an absorbent article.

BACKGROUND ART

Currently, absorbent articles such as sanitary napkins, fabric absorbent pads and incontinence pads include materials that are non-water disintegratable, and after use they are discarded in waste boxes provided in toilet rooms, requiring recovery and further disposal. However, when used absorbent articles are inadvertently flushed into flush toilets when being discarded, they can clog the pipes of the flush toilets. Research has therefore been conducted on water disintegratable materials and absorbent articles comprising them, which can be flushed into flush toilets directly after use.

In particular, when a liquid-impermeable back sheet is to be used in an absorbent article it must be impermeable to excreted fluids such as menstrual blood and urine, and because it is difficult to exhibit both liquid impermeability during use and water disintegrating property after disposal, much research has been conducted in this regard.

For example, PTL 1 describes a leak-proof sheet for a hygienic pad, wherein a water-repellent layer is layered on one side of a water-soluble resin sheet and a water disintegratable base material is layered on the other side of the water-soluble resin sheet.

That is, the leak-proof sheet described in PTL 1 has a three-layer structure with a water disintegratable base material, a water-soluble resin sheet and a water-repellent layer, being designed so that the two layers, the water-repellent layer and the water-soluble resin sheet, hold absorbed fluids inside a hygienic pad and prevent leakage.

CITATION LIST

Patent Literature

PTL 1 Japanese Unexamined Patent Publication No. 2001-333933

SUMMARY OF INVENTION

Technical Problem

However, because the leak-proof sheet described in PTL 1 contains a water-soluble resin, its use in absorbent articles is associated with the problem of significantly reduced water resistance when contacted with large amounts of moisture, when contacted with moisture for long periods, or when subjected to high humidity conditions. Furthermore, because the leak-proof sheet described in PTL 1 comprises the water-repellent layer on only one side, the other side has no leak-proof effect and sweat and other fluids infiltrating from the other side can potentially cause dissolution of the leak-proof sheet. In addition, since the leak-proof sheet of PTL 1 has a three-layer structure and requires hardening of the water-repellent layer, it is associated with problems of poor production efficiency and high cost. The leak-proof sheet described in PTL 1 also has another problem in that the water-repellent layer chemically bonds with the water-soluble resin sheet during hardening, resulting in lower water disintegrating property of the leak-proof sheet.

It is therefore an object of the present disclosure to provide a water disintegratable leak-proof sheet for an absorbent article that has an excellent leak-proof property during wear and excellent water disintegrating property after disposal.

Solution to Problem

As a result of diligent research directed toward solving the problems described above, the inventors of the present disclosure have found that the aforementioned problems can be solved by a water disintegratable leak-proof sheet for an absorbent article that comprises a water disintegratable base material layer and a water-insoluble and biodegradable resin layer on the water disintegratable base material layer, wherein the tearing strength in the planar direction of the water disintegratable leak-proof sheet is no greater than 0.15 N/40 mm in both a first direction and a second direction perpendicular to the first direction.

Advantageous Effects of Invention

The water disintegratable leak-proof sheet for an absorbent article according to the present disclosure has an excellent leak-proof property during wear and excellent water disintegrating property after disposal.

DESCRIPTION OF EMBODIMENTS

The water disintegratable leak-proof sheet for an absorbent article according to the present disclosure will now be described in detail.

Figure 1:
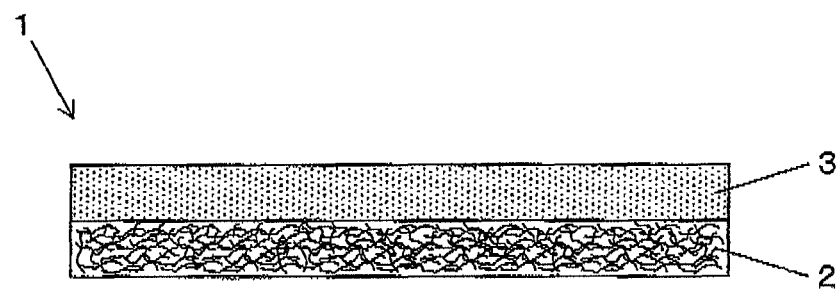
FIG. 1 is a cross-sectional view of one embodiment of the water disintegratable leak-proof sheet of the present disclosure.

The water disintegratable leak-proof sheet for an absorbent article of the present disclosure comprises a water disintegratable base material layer 2 and a water-insoluble and biodegradable resin layer 3 on the water disintegratable base material layer 2, as shown in FIG. 1.

[Water-Insoluble and Biodegradable Resin Layer]

The water-insoluble and biodegradable resin layer is a layer that imparts a leak-proof property to the water disintegratable leak-proof sheet of the invention. Since the water-insoluble and biodegradable resin layer is water-insoluble, it can exhibit water resistance when it comes close to fluids such as urine and menstrual blood from above in FIG. 1. Also, since the water-insoluble and biodegradable resin layer is water-insoluble, it can exhibit a certain degree of water resistance even when it comes close to fluids such as urine and menstrual blood from below in FIG. 1.

The resin composing the water-insoluble and biodegradable resin layer is not particularly restricted so long as it is water-insoluble and biodegradable, and resins that are known in the technical field may be employed, examples of which include polylactic acid (PLA), polybutylene succinate (PBS), polybutylene adipate/terephthalate) (PBAT), polycaprolactone (PCL), polyhydroxybutyrate (PHB) and polyhydroxyalkanoates (PHA), with polylactic acid being preferred from the viewpoint of wide distribution and cost.

Even among biodegradable resins, those that are not water-insoluble, for example, water-soluble resins such as carboxymethyl cellulose sodium (CMC) and polyvinyl alcohol (PVA), are not included among resins to compose the water-insoluble and biodegradable resin layer.

A conventional water disintegratable leak-proof sheet has a water-soluble resin coated with a water-repellent agent and thereby exhibits both water-repellency and water disintegrating property (or solubility in water), but the effect of the water-repellent agent is temporary, and although it is capable of repelling water droplets for a certain period of time it cannot maintain water-repellency for prolonged periods. Also, since a water-repellent agent cannot exhibit water-repellency against moisture such as water vapor, the water-soluble resin softens by moisture under high humidity conditions, and the leak-proof property can be impaired.

As used herein, "biodegradable" means the ability to be decomposed by the action of microorganisms.

Also as used herein, "water-insoluble" means that the solubility in 100 g of purified water at 25° C. is no greater than 1.0 g. The solubility may be judged based directly on the values listed in the published literature, or when the solubility is unknown, it may be judged by whether or not a sample whose solubility is to be measured has dissolved 24 hours after having been added to 100 g of purified water at 25° C. and gently stirred.

[Water Disintegratable Base Material Layer]

In the water disintegratable leak-proof sheet of the present disclosure, the base material of the water disintegratable base material layer is itself water disintegratable, while it also supplements the strength during production of the water disintegratable leak-proof sheet and rapidly disintegrates in water when discarded, helping to disrupt the resin composing the water-insoluble and biodegradable resin layer into fine fragments in water.

In the water disintegratable leak-proof sheet of the present disclosure, a water-insoluble and biodegradable resin may be melted and formed into a film (stratified) to form a water-insoluble and biodegradable resin layer, but considering that it is to be disrupted by the force of a water stream when discarded, the film may rupture within the continuous production line if the film thickness is too small. Therefore, the water disintegratable base material layer has the function of supplementing the strength of the water-insoluble and biodegradable resin layer and preventing rupture of the water-insoluble and biodegradable resin layer in a continuous production line.

The reason that the water disintegratable base material layer allows the resin composing the water-insoluble and biodegradable resin layer to be easily disrupted into fine fragments in water will now be explained for a case where the water disintegratable base material layer is a water disintegratable tissue.

Figure 2:
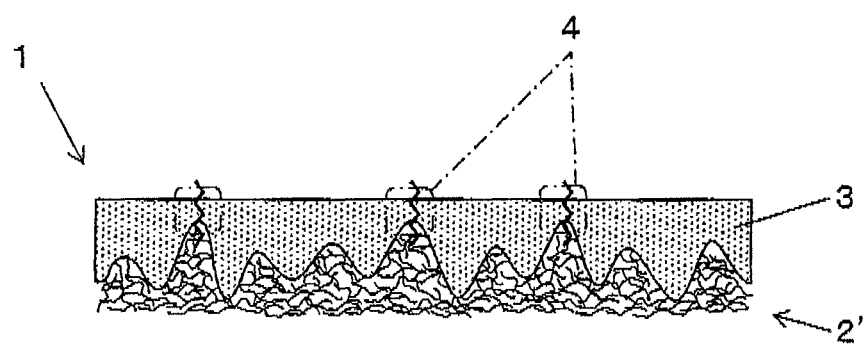
FIG. 2 is a diagram illustrating water disintegrating property of the water disintegratable leak-proof sheet of the present disclosure.

FIG. 2 is a diagram illustrating water disintegrating property of the water disintegratable leak-proof sheet of the present disclosure. The water disintegratable leak-proof sheet 1 shown in FIG. 2 comprises water disintegratable tissue 2' layer as the water disintegratable base material layer and a water-insoluble and biodegradable resin layer 3 over it. In the water disintegratable leak-proof sheet 1 shown in FIG. 2, the water-insoluble and biodegradable resin layer 3 is formed on the water disintegratable tissue 2' which is a pulp aggregate, and therefore a thickness distribution is created, so that it partially has regions of high thickness 4 and regions of low thickness.

When the water disintegratable leak-proof sheet 1 shown in FIG. 2 is discarded in water such as in a flush toilet, the water disintegratable tissue 2 rapidly disintegrates in the water. Because the water-insoluble and biodegradable resin layer 3 is water-insoluble it does not directly decompose or disintegrate in water, but since it partially has the regions of low thickness 4, the force of the water stream applied in piping or in a wastewater treatment tank causes the water-insoluble and biodegradable resin layer 3 to tear at the regions of low thickness 4 that have relatively low strength, resulting in disruption into fine fragments. The water-insoluble and biodegradable resin layer 3 that has been disrupted into fine fragments will clog pipings and wastewater treatment tanks less easily, and can be subsequently decomposed by microorganisms. FIG. 2 is a diagram for explanation of the water disintegrating property of a water disintegratable leak-proof sheet according to the present disclosure, with the film thickness distribution of the water-insoluble and biodegradable resin layer exaggerated for illustration.

The water disintegratable leak-proof sheet of the present disclosure is not limited to the embodiment shown in FIG. 2, i.e., to an embodiment wherein the water-insoluble and biodegradable resin layer has such a notable non-homogeneous film thickness, and it may instead have a homogeneous film thickness. Even if the water-insoluble and biodegradable resin layer has a homogeneous film thickness, it can still be disrupted into fine fragments by the force of a water stream.

The water disintegratable base material layer is not particularly restricted so long as it is one that is used as a water disintegratable base material in the technical field, examples of which include water disintegratable tissues, water-soluble paper and water disintegratable nonwoven fabrics, with water disintegratable tissues being preferred from the viewpoint of cost.

As used herein, "water disintegrating property" means the property of disintegrating in water when exposed to a gentle water stream, such as when it is flushed into a flush toilet, and it is a concept that includes the property of not only breaking up into the pulp units of a water disintegratable tissue or the like but also dissolving in water, i.e., water-solubility.

[Water Disintegratable Leak-Proof Sheet]

According to one embodiment of the water disintegratable leak-proof sheet of the present disclosure, the basis weight of the water disintegratable base material layer is preferably about 5 to about 25 g/m$^2$, more preferably about 7 to about 22 g/m$^2$ and even more preferably about 9 to about 20 g/m$^2$. If the basis weight is less than about 5 g/m$^2$, the function of supplementing the strength of the water disintegratable leak-proof sheet will tend to be insufficient, and if the basis weight is greater than about 20 g/m$^2$, the rigidity of the water disintegratable leak-proof sheet will tend to increase and cost efficiency will tend to be reduced.

According to one embodiment of the water disintegratable leak-proof sheet of the present disclosure, the thickness of the water-insoluble and biodegradable resin layer is about 5 to about 18 μm, more preferably about 6 to about 17 μm and even more preferably about 7 to about 16 μm. If the thickness is less than about 5 μm the leak-proof property of the water disintegratable leak-proof sheet will tend to be insufficient, and if the thickness is greater than about 18 μm, the water-insoluble and biodegradable resin layer will be more resistant to disruption by the force of a water stream, potentially leading to clogging of pipings and wastewater treatment tanks.

According to one embodiment of the water disintegratable leak-proof sheet of the present disclosure, the tearing strength in the planar direction is no greater than about 0.15 N/40 mm, preferably no greater than about 0.12 N/40 mm, even more preferably no greater than about 0.09 N/40 mm and yet more preferably no greater than about 0.06 N/40 mm in two directions, a first direction and a second direction perpendicular to the first direction. If the tearing strength is greater than about 0.15 N/40 mm, the water-insoluble and biodegradable resin layer will be more resistant to disruption by the force of a water stream, potentially leading to clogging of pipings and wastewater treatment tanks.

The tearing strength is preferably at least about 0.03 N/40 mm, to avoid rupture by the body pressure applied during wear, when it is used in an absorbent article.

The mutually perpendicular first direction and second direction are used for the tearing strength because there is a difference in tearing strength in the machine direction and the direction perpendicular to the machine direction (hereunder also referred to simply as "cross-machine direction") by the force applied during production, such as stretching force.

Thus, the first direction and second direction may be, for example, the machine direction and the cross-machine direction during production.

The tearing strength can be measured according to the "Tear test" of JIS K 6772:1994 7.5.

Throughout the present specification, the tearing strength (N) per 40 mm width will be represented as "N/40 mm".

According to one embodiment of the water disintegratable leak-proof sheet of the present disclosure, the water pressure resistance from the water-insoluble and biodegradable resin layer side is preferably at least about 300 mm, more preferably at least about 320 mm and even more preferably at least about 340 mm. If the water pressure resistance is less than about 300 mm the leak-proof property may be insufficient, potentially resulting in leakage of body fluids and the like when it is used in an absorbent article.

According to one embodiment of the water disintegratable leak-proof sheet of the present disclosure, the water pressure resistance from the water-insoluble and biodegradable resin layer side after 3 hours of storage under conditions with a temperature of 36° C. and a relative humidity of 90% is preferably at least about 300 mm, more preferably at least about 320 mm and even more preferably at least about 340 mm. If the water pressure resistance is less than about 300 mm the leak-proof property may be reduced, potentially resulting in leakage of body fluids and the like when it is used under the high-humidity conditions of an absorbent article or the like.

Throughout the present specification, the water pressure resistance after 3 hours of storage under conditions with a temperature of 36° C. and a relative humidity of 90% will also be referred to simply as "high humidity water pressure resistance", and the water resistance after 3 hours of storage under conditions with a temperature of 36° C. and a relative humidity of 90% will, also be referred to simply as "high humidity water resistance".

The water pressure resistance and high humidity water pressure resistance is the water level measured according to "Method A (Low hydraulic pressure test)" of JIS L 1092:2009 7.1.1, and more specifically, the water level at which water leaks at three locations on the back side of a test piece.

According to one embodiment of the water disintegratable leak-proof sheet of the present disclosure, the dispersion ratio after 48 hours in the shake-flask method is preferably about 50 mass % or greater, more preferably about 60 mass % or greater, even more preferably about 70 mass % or greater and most preferably 80 mass % or greater. If the dispersion ratio is less than about 50 mass, it will tend to attach to devices in wastewater treatment tanks, potentially hindering the normal functioning of wastewater treatment tanks.

The procedure for the shake-flask method is as follows.

(1) A 10 cm×10 cm square sample is placed in a 1000 mL flask containing 800 mL of distilled water and shaken in a shaker (SHKV-200, product of Iwaki) for 48 hours at a shaking speed of 240 rpm.

(2) The sample that has been subjected to the shake-flask test is filtered with a 2-mesh wire mesh (filament diameter: 1.5 mm, aperture: 11.2 mm, space factor: 77.8%), and the dispersion ratio is calculated by the following formula:

Dispersion ratio (%)=100×$(M_0-M_1)/M_0$, where $M_0$ is the dry mass of the sheet before the test and $M_1$ is the dry mass of the sheet fibers remaining on the wire mesh.

The dispersed state is visually evaluated after step (1).

The evaluation criteria are as follows.

A: Dispersed to a level such that the original form is not maintained.

B: Dispersed into three or more portions, while partially maintaining the original form.

C: The original form is maintained.

According to one embodiment of the water disintegratable leak-proof sheet of the present disclosure, an evaluation of A is most preferred, and an evaluation of B is secondarily preferred.

The method of producing the water disintegratable leak-proof sheet of the present disclosure is not particularly restricted, and according to one embodiment of the water disintegratable leak-proof sheet of the present disclosure, it may be formed by (i) adjusting the water disintegratable base material to the prescribed basis weight to form the water disintegratable base material layer, and then (ii) melt extruding the resin that is to form the water-insoluble and biodegradable resin layer onto the water disintegratable base material layer, to form a water-insoluble and biodegradable resin layer on the water disintegratable base material layer.

In the case of continuous production, when tensile force is applied to the layered stack in the machine direction after the water-insoluble and biodegradable resin layer has been formed on the water disintegratable base material layer, the water-insoluble and biodegradable resin layer is stretched in the machine direction, the crystals in the water-insoluble and biodegradable resin layer become oriented in the machine direction, and the tearing strength of the formed water disintegratable leak-proof sheet can become increased in the machine direction. For continuous production of a water disintegratable leak-proof sheet, therefore, it is preferred to avoid increasing the tensile force in the machine direction.

The water disintegratable leak-proof sheet for an absorbent article of the present disclosure can be used as a liquid-impermeable back sheet for an absorbent article. The absorbent article may be one comprising a liquid-permeable top sheet, a liquid-impermeable back sheet and an absorbent body between the liquid-permeable top sheet and liquid-impermeable back sheet, and examples of absorbent articles include sanitary napkins, panty liners, disposable diapers, incontinence pads, perspiration sheets and pet sheets.

EXAMPLES

The present disclosure will now be explained in fuller detail by examples, with the understanding that it is not meant to be limited to the examples.

Production Example 1

As a water disintegratable base material there was prepared a water disintegratable non-crepe tissue comprising 50 mass % conifer Kraft pulp (NBKP) and 50 mass % broadleaf tree Kraft pulp (LBKP), and having a basis weight of 15 g/m². As a water-insoluble and biodegradable resin layer on the water disintegratable non-crepe tissue, polylactic acid (Terramac by Unitika, Ltd.) was melt extruded at 260° C. to a film thickness of 10 μm and layered on the water disintegratable non-crepe tissue to form sheet No. 1.

Production Example 2

Sheet No. 2 was formed in the same manner as Production Example 1, except that the polylactic acid film thickness was 8 μm.

Production Example 3

Sheet No. 2 was formed in the same manner as Production Example 1, except that the polylactic acid film thickness was 15 μm.

Production Example 4

Sheet No. 4 was formed in the same manner as Production Example 1, except that the polylactic acid was changed to a blend of 70 mass % of polylactic acid (ECODEAR by Toray Co., Ltd.) and 30 mass % of polybutylene adipate/terephthalate) (ECOFLEX by BASF).
The blend was formed by mixing the different pellets, and then melt mixing the blend.

Production Example 5

Sheet No. 5 was formed in the same manner as Production Example 1, except that the polylactic acid (Terramac by Unitika, Ltd.) was changed to polybutylene succinate (GS-pla by Mitsubishi Chemical Corp.).

Production Example 6

Sheet No. 6 was formed in the same manner as Production Example 1, except that the polylactic acid (Terramac by Unitika, Ltd.) was changed to polycaprolactone (CELGREEN by Daicel Chemical Industries, Ltd.).

Production Example 7

Sheet No. 7 was formed in the same manner as Production Example 1, except that the water disintegratable non-crepe tissue was changed to a water disintegratable crepe tissue (crepe ratio: 10%) containing 50% conifer Kraft pulp (NBKP) and 50% broadleaf tree Kraft pulp (LBKP), and having a basis weight of 15 g/m².

Comparative Production Example 1

As a water disintegratable base material there was prepared a water disintegratable crepe tissue comprising 50% conifer Kraft pulp (NBKP) and 50% broadleaf tree Kraft pulp (LBKP), and having a basis weight of 15 g/m². Polyvinyl alcohol (ECOMATI AX by Nippon Synthetic Chemical Industry Co., Ltd.) was melt extruded at about 230° C. on the water disintegratable crepe tissue, to a film thickness of 18 μm. A silicone-based water-repellent agent (KS-3705 by Shin-Etsu Chemical Co., Ltd.) containing 5 mass % of a platinum catalyst was gravure printed onto the polyvinyl alcohol layer to a basis weight of 1 g/m² and irradiated with ultraviolet rays, thereby UV-curing the water-repellent agent to form sheet No. 8.

Comparative Production Example 2

Polylactic acid (ECODEAR by Toray Co., Ltd.) was formed into a film with a film thickness of 20 μm using a T-die, and then uniaxially stretched in the machine direction (draw ratio: 162%) to a film thickness of 15 μm, to form sheet No. 9 with high crystal orientation in the machine direction.

Examples 1 to 7 and Comparative Examples 1 and 2

Sheets No. 1 to 9 were evaluated in terms of sheet basis weight, tearing strength, water disintegrating property (dispersion ratio and visual), water pressure resistance and high humidity water pressure resistance. The test methods were as described above, and the water pressure resistance and high humidity water pressure resistance were the values measured from the resin layer side (water-insoluble and biodegradable). For the tearing strength there was used the average value for three measurements, for the water disintegrating property there was used the average value of three times, and for the water pressure resistance and high humidity water pressure resistance there was used the average value for five times.
The results are shown in Table 1.

TABLE 1

| Example No. | | Example 1 | Example 2 | Example 3 | Example 4 | Example 5 | Example 6 | Example 7 | Comp. Ex. 1 | Comp. Ex. 2 |
|---|---|---|---|---|---|---|---|---|---|---|
| Sheet No. | | 1 | 2 | 3 | 4 | 5 | 6 | 7 | 8 | 9 |
| Water disintegratable base material layer | Type | Water disintegratable non-crepe tissue | Water disintegratable non-crepe tissue | Water disintegratable non-crepe tissue | Water disintegratable non-crepe tissue | Mater disintegratable non-crepe tissue | Water disintegratable non-crepe tissue | Water disintegratable crepe tissue | Water disintegratable non-crepe tissue | — |
| | Basis weight (g/m²) | 15 | 15 | 15 | 15 | 15 | 15 | 15 | 15 | — |
| Non-water soluble, biodegradable resin layer | Type | PLA | PLA | PLA | PLA/PBAT | PBS | PCL | PLA | PVA + water-repellant agent | PLA |
| | Film thickness (μm) | 10 | 8 | 15 | 10 | 10 | 10 | 10 | 18 | 15 |
| Sheet basis weight | g/m² | 24.0 | 22.2 | 28.5 | 24.0 | 24.5 | 25.0 | 26.3 | 33.0 | 14.2 |
| Tearing strength | Machine direction | 0.05 | 0.04 | 0.11 | 0.06 | 0.11 | 0.14 | 0.14 | 0.15 | 0.28 |

TABLE 1-continued

| Example No. | | Example 1 | Example 2 | Example 3 | Example 4 | Example 5 | Example 6 | Example 7 | Comp. Ex. 1 | Comp. Ex. 2 |
|---|---|---|---|---|---|---|---|---|---|---|
| (N/40 mm) | Cross-machine direction | 0.06 | 0.05 | 0.12 | 0.08 | 0.10 | 0.14 | 0.06 | 0.17 | 0.14 |
| Water disintegrating property (shake flask method) | Dispersion ratio (%) | 90 | 92 | 63 | 80 | 65 | 50 | 85 | 95 | 24 |
| | Visual | A | A | B | A | B | B | A | A | C |
| Water pressure resistance | (mm) | 340 | 315 | 405 | 570 | 480 | 530 | 443 | 350 | 400 |
| High-humidity water pressure resistance | (mm) | 340 | 310 | 410 | 565 | 495 | 510 | 450 | 50 | 385 |

The water disintegratable leak-proof sheets of Examples 1 to 7 have water disintegrating property and water resistance equivalent to the leak-proof sheet of Comparative Example 1, and more excellent high humidity water resistance than the leak-proof sheet of Comparative Example 1.

The water disintegratable leak-proof sheets of Examples 1 to 7 also have a tearing strength of 0.15 N/40 mm in the machine direction and the cross-machine direction, and can be disrupted by the force of a water stream when discarded.

Specifically, the present disclosure relates to the following aspects J1 to J8.

[J1]
A water disintegratable leak-proof sheet for an absorbent article comprising a water disintegratable base material layer and a water-insoluble and biodegradable resin layer on the water disintegratable base material layer,
wherein the tearing strength in the planar direction of the water disintegratable leak-proof sheet is no greater than 0.15 N/40 mm in both a first direction and a second direction perpendicular to the first direction.

[J2]
The water disintegratable leakproof sheet according to J1, wherein the water pressure resistance from the water-insoluble and biodegradable resin layer side is at least 300 mm.

[J3]
The water disintegratable leak-proof sheet according to J1 or J2, wherein the water pressure resistance from the water-insoluble and biodegradable resin layer side after 3 hours of storage under conditions with a temperature of 36° C. and a relative humidity of 90% is at least 300 mm.

[J4]
The water disintegratable leak-proof sheet according to any one of J1 to J3, wherein the dispersion ratio after 48 hours in a shake-flask test is 50 mass % or greater.

[J5]
The water disintegratable leak-proof sheet according to any one of J1 to J4, wherein the film thickness of the water-insoluble and biodegradable resin layer is in the range of 5 to 18 μm, and the basis weight of the water disintegratable base material is in the range of 5-25 g/m².

[J6]
The water disintegratable leak-proof sheet according to any one of J1 to J5, wherein the water disintegratable leak-proof sheet is formed by layering a melted water-insoluble and biodegradable resin on the water disintegratable base material layer.

[J7]
The water disintegratable leak-proof sheet according to any one of J1 to J6, wherein the water-insoluble and biodegradable resin layer is formed from polylactic acid, and the water disintegratable base material layer is formed from water disintegratable tissue.

[J8]
An absorbent article comprising a liquid-permeable top sheet, a liquid-impermeable back sheet and an absorbent body between the liquid-permeable top sheet and liquid-impermeable back sheet,
wherein the liquid-impermeable back sheet is formed from the water disintegratable leak-proof sheet according to any one of J1 to J7.

REFERENCE SIGNS LIST

1 Water disintegratable leak-proof sheet
2 Water disintegratable base material layer
2' Water disintegratable tissue
3 Water-insoluble and biodegradable resin layer
4 Low-thickness region

The invention claimed is:

1. A water disintegratable leak-proof sheet for an absorbent article comprising a water disintegratable base material layer and a water-insoluble and biodegradable resin layer on the water disintegratable base material layer,
wherein the water disintegratable leak-proof sheet has a tearing strength in a planar direction of no greater than 0.15 N/40 mm in both a first direction and a second direction perpendicular to the first direction as measured in accordance with JIS K 6772:1994 7.5, and
the water-insoluble and biodegradable resin layer is formed from polylactic acid, and the water disintegratable base material layer is formed from water disintegratable tissue wherein the water-insoluble and biodegradable resin layer comprises regions of low thickness and regions of high thickness, and the water disintegratable base layer comprises regions of low thickness and regions of high thickness, wherein regions of low thickness in the water-insoluble and biodegradable resin layer correspond to regions of high thickness in the water disintegratable base layer, and regions of high thickness in the water-insoluble and biodegradable resin layer correspond to regions of low thickness in the water disintegratable base layer.

2. The water disintegratable leak-proof sheet according to claim 1, wherein the water disintegratable leak-proof sheet has a water pressure resistance from a side of the water-insoluble and biodegradable resin layer of at least 300 mm.

3. The water disintegratable leak-proof sheet according to claim 1, wherein the water disintegratable leak-proof sheet has a water pressure resistance from a side of the water-insoluble and biodegradable resin layer after 3 hours of storage under conditions with a temperature of 36° C. and a relative humidity of 90% of at least 300 mm.

4. The water disintegratable leak-proof sheet according to claim 1, wherein the water disintegratable leak-proof sheet has a dispersion ratio after 48 hours in a shake-flask test of 50 mass % or greater.

5. The water disintegratable leak-proof sheet according to claim 1, wherein the water-insoluble and biodegradable resin layer has a film thickness in the range of 5 to 18 μm, and the water disintegratable base material has a basis weight in the range of 5-25 g/m$^2$.

6. The water disintegratable leak-proof sheet according to claim 1, wherein the water disintegratable leak-proof sheet is formed by melting the water-insoluble and biodegradable resin layer on the water disintegratable base material layer.

7. An absorbent article comprising a liquid-permeable top sheet, a liquid-impermeable back sheet and an absorbent body between the liquid-permeable top sheet and liquid-impermeable back sheet, wherein the liquid-impermeable back sheet is formed from the water disintegratable leak-proof sheet according to claim 1.

8. The water disintegratable leak-proof sheet according to claim 2, wherein the water disintegratable leak-proof sheet has a dispersion ratio after 48 hours in a shake-flask test of 50 mass % or greater.

9. The water disintegratable leak-proof sheet according to claim 3, wherein the water disintegratable leak-proof sheet has a dispersion ratio after 48 hours in a shake-flask test of 50 mass % or greater.

10. The water disintegratable leak-proof sheet according to claim 2, wherein the water-insoluble and biodegradable resin layer has a film thickness in the range of 5 to 18 μm, and the water disintegratable base material has a basis weight in the range of 5-25 g/m$^2$.

11. The water disintegratable leak-proof sheet according to claim 3, wherein the water-insoluble and biodegradable resin layer has a film thickness in the range of 5 to 18 μm, and the water disintegratable base material has a basis weight in the range of 5-25 g/m$^2$.

12. The water disintegratable leak-proof sheet according to claim 4, wherein the water-insoluble and biodegradable resin layer has a film thickness in the range of 5 to 18 μm, and the water disintegratable base material has a basis weight in the range of 5-25 g/m$^2$.

13. The water disintegratable leak-proof sheet according to claim 9, wherein the water-insoluble and biodegradable resin layer has a film thickness in the range of 5 to 18 μm, and the water disintegratable base material has a basis weight in the range of 5-25 g/m$^2$.

14. The water disintegratable leak-proof sheet according to claim 2, wherein the water disintegratable leak-proof sheet is formed by melting the water-insoluble and biodegradable resin layer on the water disintegratable base material layer.

15. The water disintegratable leak-proof sheet according to claim 3, wherein the water disintegratable leak-proof sheet is formed by melting the water-insoluble and biodegradable resin layer on the water disintegratable base material layer.

16. The water disintegratable leak-proof sheet according to claim 4, wherein the water disintegratable leak-proof sheet is formed by melting the water-insoluble and biodegradable resin layer on the water disintegratable base material layer.

17. The water disintegratable leak-proof sheet according to claim 5, wherein the water disintegratable leak-proof sheet is formed by melting the water-insoluble and biodegradable resin layer on the water disintegratable base material layer.

* * * * *